United States Patent
Toker et al.

(10) Patent No.: US 6,678,546 B2
(45) Date of Patent: Jan. 13, 2004

(54) MEDICAL INSTRUMENT GUIDANCE USING STEREO RADIOLOCATION

(75) Inventors: Emre Toker, Tucson, AZ (US); Morgan W. Nields, Englewood, CO (US)

(73) Assignee: Fischer Imaging Corporation, Denver, CO (US)

( * ) Notice: Subject to any disclaimer, the term of this patent is extended or adjusted under 35 U.S.C. 154(b) by 28 days.

(21) Appl. No.: 09/772,558

(22) Filed: Jan. 30, 2001

(65) Prior Publication Data

US 2002/0103431 A1 Aug. 1, 2002

(51) Int. Cl.⁷ .................................................. A61B 8/00
(52) U.S. Cl. ...................................................... 600/436
(58) Field of Search ................................. 600/436, 568, 600/407; 128/659; 606/45; 250/214 A, 214 R

(56) References Cited

U.S. PATENT DOCUMENTS

| | | | | |
|---|---|---|---|---|
| 4,521,808 A | * | 6/1985 | Ong et al. ..................... | 378/29 |
| 4,550,597 A | * | 11/1985 | Drutchas et al. ............ | 73/118.1 |
| 5,273,043 A | | 12/1993 | Ruike ......................... | 128/659 |
| 5,464,013 A | * | 11/1995 | Lemelson ................... | 600/427 |
| 5,694,933 A | * | 12/1997 | Madden et al. ............. | 600/431 |
| 5,732,704 A | | 3/1998 | Thurston et al. ............ | 128/659 |
| 5,810,806 A | | 9/1998 | Ritchart et al. .............. | 606/45 |
| 5,857,463 A | | 1/1999 | Thurston et al. ............ | 128/659 |
| 5,928,150 A | | 7/1999 | Call ............................ | 600/436 |
| 5,961,458 A | | 10/1999 | Carroll ....................... | 600/436 |
| 6,021,341 A | | 2/2000 | Scibilia et al. .............. | 600/407 |
| 6,022,325 A | | 2/2000 | Siczek et al. ............... | 600/568 |
| 6,135,955 A | * | 10/2000 | Madden et al. ............. | 600/436 |
| 6,195,580 B1 | * | 2/2001 | Grable ........................ | 600/473 |
| 6,210,317 B1 | * | 4/2001 | Bonlie ........................... | 600/9 |
| 6,296,613 B1 | * | 10/2001 | Emmenegger et al. ...... | 600/459 |
| 6,312,393 B1 | * | 11/2001 | Abreu ......................... | 600/558 |
| 6,331,700 B1 | * | 12/2001 | Wake et al. ............. | 250/208.1 |
| 6,339,216 B1 | * | 1/2002 | Wake ...................... | 250/214 A |
| 6,490,467 B1 | * | 12/2002 | Bucholz et al. ............. | 600/407 |

* cited by examiner

*Primary Examiner*—Sang Y. Paik
*Assistant Examiner*—Daniel L. Robinson
(74) *Attorney, Agent, or Firm*—Marsh Fischmann & Breyfogle LLP

(57) ABSTRACT

A stereo radiolocalization and targeting system (100) includes a table assembly (102) for supporting a patient (104), a stereo radiolocalization subsystem (117), a medical instrument support subsystem (119), and an ultrasound imaging subsystem (121). The stereo radiolocalization subsystem (117) provides three-dimensional localization information for an area of interest within the patient's body such as a sentinel node. The medical instrument support subsystem (119) allows for targeting of a medical instrument (118) to the area of interest for treatment, extraction or other procedures. The imaging subsystem (121) provides real-time imaging for use in penetration path selection and monitoring medical instrument insertion. Flexible positioning support mechanisms (120, 122, and 124) provide substantial positioning flexibility for various elements of the system (100).

13 Claims, 2 Drawing Sheets

MEDICAL INSTRUMENT GUIDANCE USING STEREO RADIOLOCATION

FIELD OF THE INVENTION

The present invention relates in general to medical instrument guidance for minimally invasive medical procedures and, in particular, to three-dimensional guidance using stereo radiolocation and related imaging for penetration path selection. The present invention has particular advantages with respect to sentinel node biopsy procedures.

BACKGROUND OF THE INVENTION

The use of radioactively tagged materials for medical imaging, tissue identification and certain localization procedures is well-established. One such application relates to identification of a sentinel node in connection with the staging and treatment of breast cancer. Determining whether cancer has spread from a mass within the breast to the lymph nodes, generally located near the patient's armpit, is important in selecting a course of treatment and establishing a definitive prognosis. In this regard, a radioactively tagged material or radiopharmaceutical may be utilized to assist in locating the sentinel node.

Generally, the radiopharmaceutical is injected near the site of a cancerous mass within the patient's breast and then drains to the sentinel node. The injection may alternatively be made subdermally or periareolarly. A photon detector such as a hand-held probe can then be used to locate the sentinel node by manually moving the probe over the armpit area while monitoring detector readings to identify a radiation peak. Such probes have been used to guide surgeons to the site of the sentinel node and it has further been proposed to use such probes in connection with certain medical instruments for minimally invasive sentinel node extraction.

While such procedures or proposals represent a significant advance in the diagnosis and treatment of breast cancer, a number of challenges remain with respect to full realization of the associated potential benefits. First, given the gravity of the medical context, accurate identification and localization of the sentinel node is essential to provide physicians with the confidence necessary to rely on such procedures in making diagnoses and establishing courses of treatment. However, because the detector is hand-held, the photon detector may have limited accuracy in localizing the node. In addition, there is no ability to correlate, to the required accuracy, the probe location to the location of any separate instrument used for extraction. Moreover, minimally invasive procedures are hampered by a concern for damaging nerves or other sensitive tissue that is present in the vicinity of the sentinel node during penetration of the medical instrument into the axilla. Accordingly, surgical node removal remains the standard, in part because open surgical removal allows the surgeon to avoid damage to such sensitive tissues.

SUMMARY OF THE INVENTION

The present invention is directed to three-dimensional localization of an area of interest within a patient's body for instrument guidance based on photon/radiation emissions. The invention thus allows for accurate determination of the spatial coordinates of the area of interest identified based on emissions therefrom, for example, as a result of using a radioactive material or radiopharmaceutical. Such coordinates can be used in accordance with the present invention to guide a medical instrument to the identified location, for example, for treatment, sampling or extraction. The invention also provides for spatially correlated imaging to facilitate penetrate path selection. Moreover, the invention enables flexible positioning of one or more photon detectors, imaging probes, and medical instruments while maintaining identifiable positions relative to a known frame of reference so as to facilitate localization and targeting of difficult to access areas of interest, as well as penetration path selection.

In accordance with one aspect of the present invention, the spatial location of an area of interest within a patient's body is identified relative to a predetermined frame of reference by radiolocalization. An associated apparatus includes: a patient support for supporting the patient in a substantially fixed position relative to a predetermined frame of reference; a photon detector system for receiving photon emissions from an area of interest within the patient's body and providing location information based on the emissions; and a processor for identifying the three-dimensional spatial location of the area of interest relative to the predetermined frame of reference based on the location information from the photon detector system.

It will be appreciated that identifying the location of the area of interest relative to a predetermined reference or concurrent frame facilitates subsequent or concurrent medical instrument targeting, imaging or other procedures. In one embodiment, a multiple pin hole collimator is used in conjunction with a single gamma camera to generate the location information so as to provide three-dimensional data. Alternatively, two or more detectors may be used for stereo radiolocation based on gamma radiation, visible light, near infrared or infrared photon emissions. In the latter case, the photon detector system may include a first photon detector, mounted in known spatial relationship and moveable with respect to the predetermined frame of reference, for providing first information regarding the position of an area of interest within the patient's body based on photons emitted from the area of interest; and a second photon detector, mounted in known spatial relation and movable with respect to the predetermined frame of reference, for providing second information regarding the position of the area of interest within the patient's body based on photons emitted from the area of interest. In this latter case, it will be appreciated that each of the photon detectors can provide directional information regarding the area of interest based on radiation propagating from the area of interest. Thus, in this case, by using two photon detectors that provide spatially correlated information, three-dimensional coordinates can be determined regarding the location of interest thereby facilitating localization, e.g., for instrument guidance.

In accordance with another aspect of the present invention, a medical instrument is guided to an area of interest within the patient's body based on radiolocation. An associated apparatus comprises: a patient support for supporting a patient in a substantially fixed position relative to a predetermined frame of reference; at least one photon detector, mounted in known spatial relation and movable relative to said predetermined frame of reference, for providing position information regarding the area of interest based on photons emitted therefrom; a medical instrument support, located in predetermined spatial relation and movable and relative to said predetermined frame of reference, for use in targeting a medical instrument at the area of interest; and a processor for receiving first information regarding the location of the area of interest, receiving second information regarding a position of the medical instrument and providing guidance information for use in targeting the medical instrument at the area of interest. By mounting the medical instrument support and the photon detector(s) in a spatially correlated manner relative to the patient support, radiolocalization information can be used for targeting a medical instrument to a location of interest within the patient's body.

According to a still further aspect of the present invention, a substantially real-time imaging system is used in connection with a radiolocalization device for selection of a penetration path for targeting an area of interest with a patient's body. The radiolocalization device is utilized to determine the spatial location of the area of interest with the patient's body relative to a predetermined frame of reference. The real-time imaging system includes an imaging element that is mounted in known spatial relation and movable relative to the predetermined frame of reference for providing real-time images that can be used for penetration path selection. Preferably, a curser or other marker indicating the calculated location of the source of radio emissions is superimposed on a display of the real-time imaging system to identify the area of interest. A physician can then use the real-time images to select a penetration path to the identified area of interest while avoiding sensitive tissues that may be interposed between the skin of the patient and the area of interest. Real-time imaging also provides a confirmation to the physician that the calculated source of radio emissions coincides with the area of interest displayed by the real-time imaging system. The object targeted by the radio labeled agent is likely visible by the type of real time imaging system selected.

According to a still further aspect of the present invention, a support assembly, positionable in three-dimensional space, is used to facilitate radiation based instrument guidance. The flexible positioning system, in one implementation, is used in connection with a medical instrument guidance device that includes: a support for supporting a patient in known spatial relation relative to a predetermined frame of reference; one or more photon detectors, mounted in known spatial relation and movable relative to the predetermined frame of reference, for identifying a position of the area of interest based on the photons emitted therefrom; a medical instrument support, mounted in known spatial relation and movable relative to the predetermined frame of reference, for supporting a medical instrument for use in penetrating to the area of interest; and an imaging element, mounted in known spatial relation to and movable relative to the predetermined frame of reference, for providing imaging that can be used for penetration path selection. One or more of the photon detector, medical instrument support, and imaging element may be supported using the flexible positioning system in accordance with this aspect the invention.

The flexible positioning system includes a support for supporting a detector, imaging element or medical instrument as noted above. The system further includes a first positioning mechanism for allowing movement of the support in three spatial dimensions and a second positioning mechanism for allowing angular positioning of the support. Preferably, the second mechanism allows for angular positioning relative to two transverse reference planes. The system further includes a subsystem for tracking the spatial and angular position of the support. The spatial position and angular position may be tracked using encoders, magnetic field devices, radio frequency (RF) transmitters and antennae/receivers or other appropriate means. Alternatively, where the support supports an imaging element, feedback regarding the targeting position may be obtained based on the imaging information received from the imaging element. The flexible positioning element thereby facilitates targeting of a medical instrument in difficult to access areas such as an armpit region of a patient, e.g., for sentinel node identification and targeting, and facilitates penetration path selection. This element also allows for penetration path selection in relation to penetrating the abdomen of a patient in such a manner as to minimize injury to the patient's vascular, lymphatic and nervous systems as well as vital patient organs.

BRIEF DESCRIPTION OF THE DRAWINGS

For a more complete understanding of the present invention and further advantages thereof, reference now made to the following Detailed Description taken in conjunction with the drawings in which.

DETAILED DESCRIPTION

Figure 1:
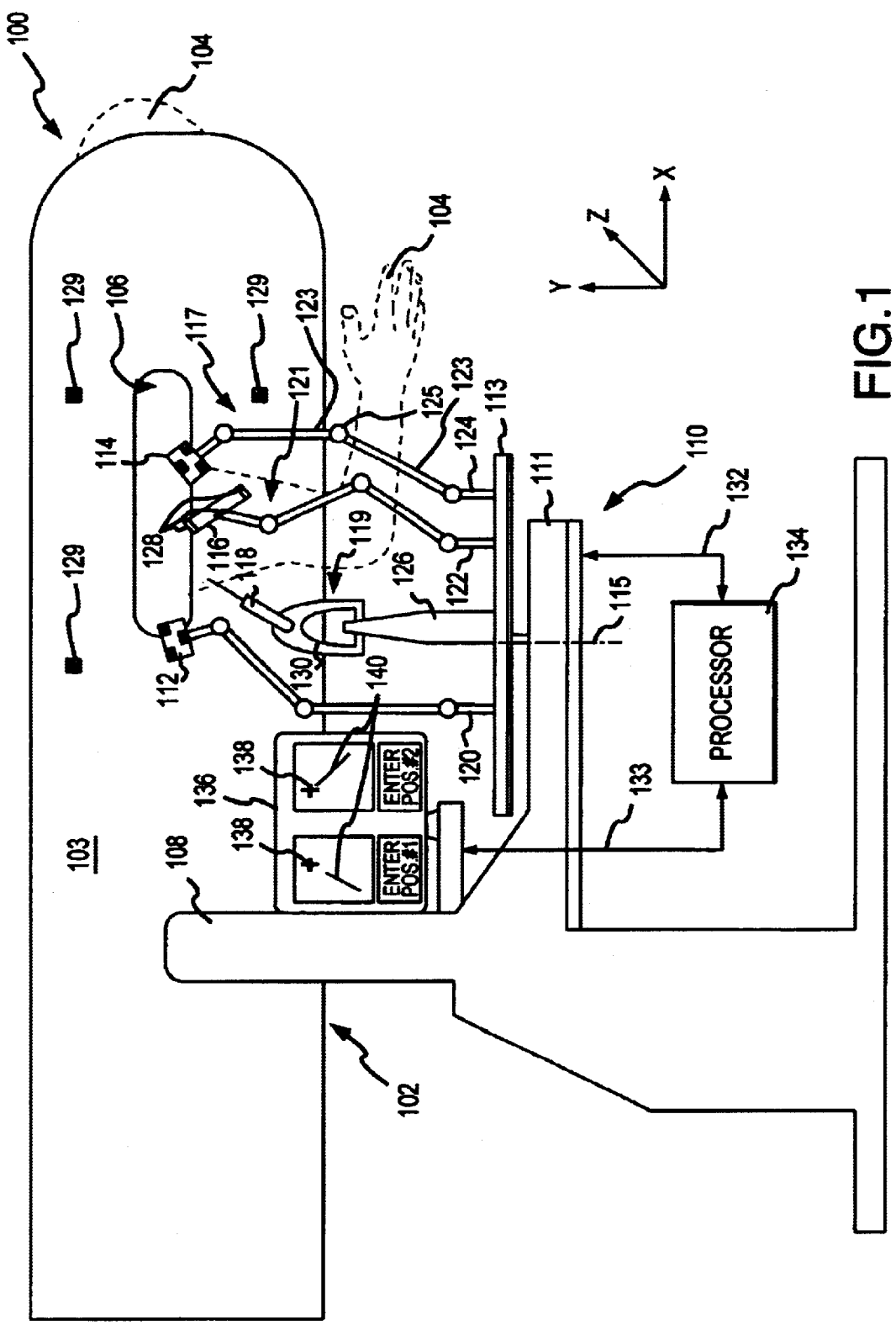
FIG. 1 is a perspective view of a stereo radiolocalization and targeting system in accordance with the present invention.

FIG. 1 illustrates a stereo radiolocalization and targeting system in accordance with the present invention. The illustrated system 100 represents a preferred embodiment of the invention illustrating various aspects of the invention in connection with one application thereof; namely a sentinel node application. It will be appreciated however that many other implementations are possible and certain aspects of the invention have independent utility as well as utility for applications other than sentinel node targeting and extraction.

In the illustrated embodiment the system 100 includes a table assembly 102 for supporting a patient 104 in a prone position. It will be appreciated that the patient 104 may alternatively be supported in an upright or other position rather than prone as shown. However, for sentinel node targeting and extraction, it is important to immobilize the patient and prone positioning yields certain advantages in this regard.

The table assembly 102 includes a tabletop 103, a support pedestal 108 and a support arm assembly 110. The tabletop 103 includes an opening 106 to provide access to the patient 104 by various medical devices mounted beneath the tabletop 103. The support arm assembly 110 includes a first support arm 111 and a second support arm 113. The second support arm 113 is mounted on the first support arm 111 for rotation about axis 115 so as to permit additional flexibility with regard to approach angles for imaging and targeting the patient 104. The table assembly 102 may be, for example, the Mammotest table marketed by Fischer Imaging Corporation of Denver, Colo.

In the illustrated embodiment, the support arm assembly 110 supports a number of medical device subsystems. The subsystems include a stereo radiolocalization subsystem 117, a medical instrument support subsystem 119 and an ultrasound imaging subsystem 121. Each of these subsystems is described in turn below.

The stereo radiolocalization subsystem 117 provides three-dimensional localization information for an area of interest within the patient's body, in this case, a sentinel node. As noted above, identifying the sentinel node and extracting the node has become an important part of breast cancer diagnosis and treatment. In order to identify the sentinel node, a radiopharmaceutical may be injected near a cancerous mass within the patient's breast. The radiopharmaceutical will then drain to the sentinel node. The sentinel node is generally located in the patient's axilla, located in the armpit region. It should be appreciated that the sentinel node may be variable in size I, for example, ranging from the size of a small pea to a walnut. Accordingly, in order to enable targeting of a medical instrument for minimally invasive extraction, it is important to accurately determine the three-dimensional coordinates of the sentinel node.

The subsystem 117 provides an ability to calculate three-dimensional locational information regarding the sentinel node within the axilla or elsewhere in the body. In this regard, it is possible to use a single gamma camera in connection with a multiple pin hole collimator to provide such information. The illustrated subsystem 117 includes first and second flexible positioning support assemblies 120 and 124 mounted on the support arm assembly 110. It will be appreciated that mounting the assemblies 120 and 124 in fixed relation to the table assembly 102 on the second support arm 113 yields a number of advantages. First, by mounting the assemblies 120 and 124 on the table assembly 102 the spatial relationship between the assemblies 120 and 124, on the one hand, and the table assembly 102, on the other hand, can be conveniently calculated and maintained. Since the patient 104, in turn, maintains a substantially fixed position relative to the table assembly 102 during the procedure, the spatial coordinates of the sentinel node determined by the subsystem 117 can be readily correlated to the spatial position of a medical instrument (also mounted in known spatial relationship to the table assembly 102 as described below).

The flexible support assemblies 120 and 124 carry photon detectors 112 and 114. As will be described in more detail below, the assemblies 120 and 124 allow for convenient manipulation of the spatial and angular position in three dimensional space of the detectors 112 and 114 by a physician. The photon detectors 112 and 114 each provide information regarding the location of the sentinel node based or detection of photons emitted by the radiopharmaceutical or other photon emitting agent that has drained to the node. Specifically, one or both of the detectors 112 and 114 can be moved over the patient's body in the vicinity of the sentinel node while monitoring a detector output. When the detector output reaches a peak value, the detector 112 or 114 is centered over the sentinel node and is directed and focused at the sentinel node. Thus, in effect, each of the detectors 112 and 114, considered alone, can be centered on a ray extending from the location of the sentinel node. Once two such rays are identified using the two detectors 112 and 114, the three-dimensional coordinates of the sentinel node can be determined using well-known mathematical techniques such as triangulation. For example, in a simple form, each of the rays emanating from the sentinel node can be represented as a line within in the XYZ coordinate system as illustrated. Simultaneously solving the equations representing the two lines will yield a single point of intersection which provides the XYZ coordinates of the sentinel node. Alternatively, one detector with an appropriate collimator can be used to calculate the spatial coordinates of the rays emanating from the area of interest.

The illustrated system 100 also includes a medical instrument support subsystem 119 for supporting a medical instrument 118. The nature of the medical instrument will depend on the particular application. For example, in various medical contexts, it may be desired to target an identified area of interest with a biopsy needle, to insert a cannula or other instrument to the area of interest for injecting a pharmacological or biological agent, medicament or radiopharmaceutical, to insert a fiber optic endoscope to the area of interest for visualization purposes or to access the area of interest for ablation of other types of treatment. In the illustrated application, the medical instrument 118 is a tissue extraction instrument. Preferably, the instrument 118 includes a relatively narrow gauge cannula or hollow needle. A tissue extraction mechanism can be inserted through the cannula to the area of interest. As the tissue extraction element approaches the area of interest, the extraction element opens to a deployed position for harvesting the sentinel node as well as, perhaps, some of the tissue surrounding the sentinel node. The extraction element can then be closed and retracted through the narrow gauge cannula. A number of such instruments are currently being developed or marketed including, for example, instruments of SenoRx Corporation of California and Neothermia Corporation of Massachusetts.

The medical instrument support subsystem 119 is mounted on a support arm 126 which in turn is mounted on the arm assembly 110. Accordingly, the position of the medical instrument can be readily correlated to the coordinates of the sentinel node as determined by the stereo radiolocalization subsystem 117. The illustrated support subsystem 119 is operative for targeting the medical instrument 118 in three-dimensions. Such targeting may be accomplished by linear and/or angular movements. In the illustrated embodiment the assembly 119 is linearly movable in three spatial dimensions, e.g., the XYZ dimensions as illustrated. One or more of these movements may be motorized and controlled in response to signals from a controller as described below. In addition, the medical instrument 118 is moveable in forward and reverse directions for insertion to the area of interest and retraction therefrom. The subsystem 119 may be angularly moveable in at least one dimension, e.g., the YZ plane of the illustrated embodiment. Moreover as noted above, the subsystem 119 is mounted on arm 113 which can be rotated relative to arm 111 for different approach angles relative to the patient. The illustrated support subsystem 119 may be, for example, the medical instrument support assembly currently provided on the Mammotest subsystem marketed by Fischer Imaging Corporation of Denver, Colo.

It will be appreciated that the localization subsystem 117 in combination with the medical instrument support subsystem 119 can be used to identify the coordinates of the sentinel node and to insert a medical instrument 118 to extract the sentinel node. However, it is also desirable to provide for substantially real-time imaging to select a penetration path for targeting the sentinel node. In this regard, it will be appreciated that the vicinity of the sentinel node typically includes a variety of nerves and other sensitive structures such as blood vessels that could be damaged if traversed by the medical instrument 118. Various substantially real-time imaging technologies may be utilized to select a penetration path that is likely to avoid such tissues. One such imaging technology is ultrasound imaging as employed in the illustrated embodiment. For example, ultrasound imaging may be used to identify a penetration path that avoids arteries. Since such arteries are often coincident with nerves or other sensitive material, viewing and avoiding the arteries allows the medical instrument 118 to penetrate to the sentinel node with a reduced likelihood of undesired tissue damage. Other types of imaging probes include fiber optic endoscopes using visible, near infrared or infrared optical imaging signals for localized imaging. X-ray imaging may also be employed particularly for orientation relative to anatomical landmarks such as bones.

The illustrated imaging subsystem 121 includes an ultrasound probe assembly 116 carried by a flexible positioning support 122. The imaging probe 116 preferably includes an array of ultrasound imaging elements as described in co-pending U.S. patent application Ser. No. 09/449,267 which is incorporated herein by reference. Preferably, the imaging device 116 can be manipulated to contact the patient at a desired orientation relative to the desired penetration path of the medical instrument so that penetration of the instrument can be monitored in real-time. The flexible support assembly 122 allows for substantial flexibility for spatial and angular positioning in this regard.

As will be appreciated from the foregoing, substantial positioning flexibility may be desired for various elements for the system 100 including, in the illustrated embodiment, each of the detectors 112 and 114 and the imaging device 116. This is provided in the illustrated embodiment by the flexible positioning support mechanisms 120, 122, and 124. Because each of these assemblies 120,122, and 124 are functionally similar, only assembly 120 is described in detail below.

Figure 2:
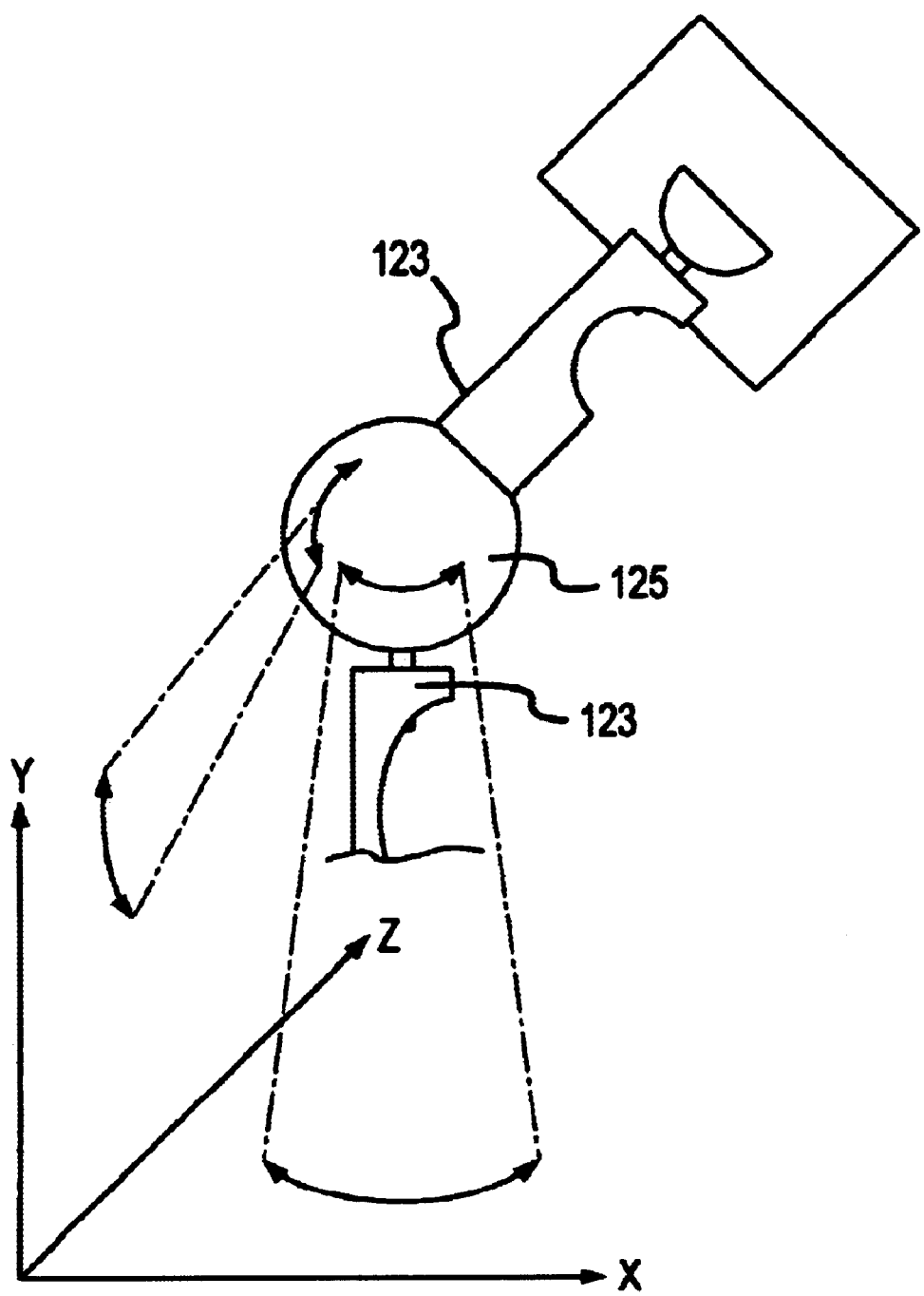
FIG. 2 is a perspective view of a portion of a flexible positioning support assembly in accordance with the present invention.

The illustrated assembly 120 is an articulated arm formed by a number of segments 123 connected at preferably two or more ball joints 125. As shown in FIG. 2 each of the ball joints 125 allows relative angular rotation as between adjacent segments 123 with reference to two transverse planes, e.g., the XZ plane and the YZ plane. Preferably, such rotation of the ball joint 125 is free enough so that a physician can easily position the supported device both spatially and angularly by simply moving the device to a desired location relative to the patient 104. On the other hand, the ball joints 125 are preferably rigid enough once positioned so that the physician can release the supported device and it will maintain its location for convenient hands-free operation. Such ball joints 125, which typically move in a ratcheting motion, are well-known for use in other applications. For example, the illustrated articulated arm may be the MicroScribe 3D model marketed by Immersion Corporation.

It is also important to know the locations of at least the detectors 112 and 114 and the medical instrument 118 so that these positions can be correlated to permit accurate targeting of the medical instrument 118 to the coordinates of the sentinel node as determined using the detectors 112 and 114. The position of the medical instrument 118 is determined by feedback encoders associated with the positioning elements of the support subsystem 119 as implemented in the current Mammotest table marketed by Fischer Imaging Corporation of Denver, Colo. Such positioning is indexed to a reference frame that is fixed relative to the patient table assembly 102.

The positions of the detectors 112 and 114 may be determined in various ways. For example, optical encoders or other position feedback elements may be associated with the various ball joints 125 and/or elements 123 to provide a cumulative indication of the position of the supported device as is common in the field of robotics. Alternatively, more sturdy support arms may be used to support the weight of the detectors or other components and precision articulated arms with encoder feedback may be attached to the detectors or other components for providing position information (without significant structural support). As a further alternative, the location of the detectors 112 and 114 may be determined based on analysis of radiomagnetic signals from the detectors 112 and 114. In this regard, the detectors may be located based on a magnetic field analysis, by tracking LEDs associated with the detectors 112 and 114 using a CCD camera or by tracking FR emitters. In the illustrated embodiment, the location of the detectors 112 and 114 is determined based on radio signals. In this regard, a number of radiotransmitters 128 (preferably at least three) are mounted on the detector 112. Each of these RF transmitters 128 provides an identifiable RF signal. For example, each of the transmitters 128 may utilize a different frequency or provide a signal that is encoded to identify the particular transmitter. The signals may then be detected by RF detectors 129 provided at known locations relative to the reference frame of the patient table assembly 102, for example, mounted underneath the table 103. Based on the time delay of arrival, angle of arrival, or other parameters of the RF signals received by the various detectors 129, the location of each transmitter can be accurately determined using known geometric techniques, including ranging and triangulation.

Based on a determination of a location of each of the transmitter elements 128 associated with a given device, as well as the known spatial relationship of each of the transmitters 128 relative to the device, the spatial position and angular orientation of the device can be accurately determined. In the illustrated embodiment, such RF locating technology is used to identify the location of each of the detectors 112 and 114 and may also be used to locate the imaging device 116. Alternatively, the imaging device 116 may be properly positioned by a physician based on visual feedback by viewing a monitor 138, preferably mounted underneath the table 103, or otherwise accessible for viewing from beneath the table 103. Thus, the physician may move the imaging over the patient's anatomy until an image of the medical device 140 can be viewed in real time during insertion. By monitoring the medical instrument 118 during insertion, correction to the penetration path can be made to avoid sensitive tissue.

Penetration path selection can be implemented in a variety of ways. For example, the medical device support assembly 119 may be mounted relative to the rotation axis 115 such that the approach angle of the medical instrument 118 relative to the patient can be altered while maintaining the medical instrument 118 in an appropriate position for targeting the sentinel node. Alternatively, the support element 126 associated with the medical instrument 118 can be moved to various locations and the appropriate coordinates for targeting of the medical instrument 118 can be recalculated until an acceptable penetration path is identified.

FIG. 1 also shows a processor 134 interconnected to the various devices by line 132 and to the monitor by line 133. The processor 134 is operative for receiving location and imaging information from the various devices and for outputting imaging and location information to the monitor 136. In this regard, the processor 134 provides positioning information to the medical instrument support subsystem 119 and, if desired, the imaging subsystem 116. This positioning information can be used to properly position the medical instrument 118 and imaging device 116.

The processor 134 also provides location and imaging information to the monitor 136. The location information allows a curser or the like to be superimposed on the image or images displayed on the monitor 136 so that the physician can monitor the approach of the medical instrument 118 to the sentinel node.

In operation, a sentinel node localization, targeting and extraction procedure in accordance with the present invention can be implemented as followed. First, a radiopharmaceutical is injected near to a cancerous mass within the patient's breast in conventional fashion. The radiopharmaceutical drains to the sentinel node. The patient is then positioned on the table 103 with the patient's arm extending through the opening 106 such that the patient's armpit region can be accessed from beneath the table. Handles or the like may be mounted on the table to facilitate proper positioning of the patient's arm. The physician then positions one of the detectors 112 and 114 over the sentinel node. This might be accomplished, for example, by moving the detector while concurrently watching a detector readout in order to identify a radiation peak. Once the first detector 112 or 114 is properly positioned, the physician inputs this position information, for example, by way of a mouse click on an appropriate graphical object of a graphical user interface computer system. In a two detector configuration, this process is then repeated for the other detector 112 or 114. Based on these inputs, the processor 134 determines the spatial coordinates of the sentinel node.

Based on these spatial coordinates, the medical instrument 118 can be targeted at the sentinel node. In particular, the computer may direct one or more motors to position the medical instrument 118 at the correct position and angular orientation. Optionally, movements relative to one or more dimensions may be made manually. The imaging device 116 is also positioned for proper viewing of a proposed penetration path. Again, such positioning may be motorized or manual. The physician can then view the monitor 136 to determine whether the proposed penetration path is acceptable. In this regard, the proposed penetration path may be graphically superimposed on the images displayed on the monitor 136. If the penetration path is acceptable, the physician can initiate the insertion of the medical instrument 118 to the sentinel node while monitoring such insertion in real-time on the monitor 136 to ensure accurate targeting.

If the position penetration path is not acceptable a new proposed penetration path may be selected, for example, by rotating arm 113 relative to arm 111. The medical instrument support subsystem 119 is preferably isocentrically mounted on arm 113 relative to arm 111 such that the medical instrument remains targeted at the sentinel node when arm 113 is rotated and only the penetration path changes. This process can be repeated until an acceptable penetration path is identified.

The physician then inserts the medical instrument to a location adjacent to the sentinel node. The medical instrument 118 can then be deployed to harvest the sentinel node as required and, perhaps, some surrounding tissue. Finally, the medical instrument 118 is retracted and the harvested material is used in conventional fashion for establishing a diagnosis in course of treatment.

It will be appreciated that various aspects of the invention as described above are applicable in contexts other than sentinel node biopsies or treatment. For example, an agent that emits signals may be introduced into an organ of a patient. A suitable signal detector mechanism as described above may then be used to overlay a location marker or image on a real time image of a separate imaging system, such as an ultrasound image for real time visualization, used for instrument guidance. It is anticipated that a doctor targeting the instrument to the organ will be able to identify the organ on the image based on appearance. Alternatively, the overlay image portion may be highlighted in some manner in the digital processing. In this manner, the organ may be targeted using the organ emissions based image portion by keeping the instrument pointed at the organ and the additional imaging information can be used for penetration path selection and real time monitoring of instrument insertion.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. An apparatus for use in performing a medical procedure on an area of interest within a patient's body, comprising:
    a patient support for supporting said patient in a substantially fixed position relative to a predetermined frame of reference;
    a photon detector system, disposed in known spatial relation to and moveable with respect to said predetermined frame of reference, for receiving photon emissions from the area of interest within the patient's body and providing location information relative to said predetermined frame of reference based on the emissions, wherein a source of said photon emissions is within said patient's body and said source emits photons in multiple non-collinear directions from said source; and
    a processor for receiving the location information from said photo detector system and identifying three-dimensional spatial coordinates of the area of interest relative to said predetermined frame of reference based on the location information.

2. An apparatus as set forth in claim 1, wherein said patient support includes means for supporting said patient in a prone position.

3. An apparatus as set forth in claim 1, wherein said patient support includes a table having an opening, wherein said photon detector system includes at least one detector element positionable beneath said table for accessing said patient via said opening.

4. An apparatus as set forth in claim 1, wherein said photon detector system comprises a gamma camera and a multiple pin hole collimator, said camera and collimator being cooperatively operative for providing said location information.

5. An apparatus as set forth in claim 1, wherein said photon detector system includes:
    a first photon detector, mounted in known spatial relation to and moveable with respect to said predetermined frame of reference, for providing first information regarding said location of the area of interest; and
    a second photon detector, mounted in known spatial relation to and moveable with respect to said predetermined frame of reference for providing second information regarding said location of the area of interest.

6. An apparatus as set forth in claim 5, wherein said processor is operative for using said first information, said second information and known geometric relationships involving the positions of each of said first and second detectors to determine said three-dimensional spatial coordinates of the area of interest.

7. An apparatus as set forth in claim 5, further comprising means for determining the position of each of said first and second photon detectors.

8. An apparatus as set forth in claim 7, wherein said means for determining comprises one of a position encoder and a radio frequency location unit associated with said first and second photon detectors.

9. An apparatus as set forth in claim 1, further comprising a medical instrument support assembly mounted in known spatial relation to and moveable relative to said predetermined, frame of reference for targeting a medical instrument to said location of interest identified by said processor.

10. An apparatus as set forth in claim 9, wherein said medical instrument support assembly includes a penetration path selection subassembly for allowing for selection as between a plurality of different paths for targeting said medical instrument wherein, for each said path, said medical instrument is targeted at said area of interest.

11. An apparatus as set forth in claim 1, further comprising a substantially real-time imaging system including a monitor, positionable for viewing by a physician performing said medical procedure on said patient, for providing an image of a portion of said patients body including said location of interest.

12. An apparatus as set forth in claim 11, wherein said monitor is mounted on said patient support.

13. An apparatus as set forth in claim 11, wherein said processor and said imaging system are operatively interconnected so as to allow for display of a marker indicative of said spatial location of the area of interest.

* * * * *